United States Patent [19]

Trivedi

[11] Patent Number: 4,780,464

[45] Date of Patent: Oct. 25, 1988

[54] (1,2,4)TRIAZOLO(4,3-A)QUINOXALINE-4-AMINES

[75] Inventor: Bharat K. Trivedi, Canton, Mich.

[73] Assignee: Warner-Lambert Company, Morris Plains, N.J.

[21] Appl. No.: 939,212

[22] Filed: Dec. 8, 1986

[51] Int. Cl.$^4$ .................. C07D 487/04; C07D 241/44; A61K 31/495; C07B 39/00
[52] U.S. Cl. ...................................... 514/250; 544/346
[58] Field of Search .......................... 514/250; 544/346

[56] References Cited

U.S. PATENT DOCUMENTS

| 4,242,344 | 12/1980 | Lumma | 544/350 |
| 4,495,187 | 1/1985 | Sarges | 514/250 |
| 4,623,725 | 11/1986 | Kadin | 544/346 |

FOREIGN PATENT DOCUMENTS 181282  9/1985  European Pat. Off. .

OTHER PUBLICATIONS

Snyder et al., Proc. Natl. Acad. Sci 78, 3260 (1981).
Ukena, Fed. Europ. Bio. Chem. Soc 209, 122 (1986).

*Primary Examiner*—Mark L. Berch
*Attorney, Agent, or Firm*—Elizabeth M. Anderson

[57] ABSTRACT

A unique series of [1,2,4]triazolo[4,3-a] quinoxaline-4-amine derivatives which show excellent binding affinity at both the $A_1$ and $A_2$ adenosine receptor sites. The compounds are useful in treating depression, fatigue, and heart failure. Also disclosed are methods for preparing the compounds, compositions containing the compounds and methods for using them.

4 Claims, No Drawings

(1,2,4)TRIAZOLO(4,3-A)QUINOXALINE-4-AMINES

BACKGROUND OF THE INVENTION

The compounds of the invention are a series of novel [1,2,4]triazolo[4,3-a]quinoxaline-4-amine derivatives which are useful as antidepressants, antifatigue agents, and for increasing myocardial contractility. These novel compounds show excellent binding affinity at both the $A_1$ and $A_2$ adenosine receptor sites with a high degree of selectivity for the $A_1$ receptor site.

U.S. Pat. No. 4,547,501 discloses certain [1,2,4]triazolo[4,3-a]quinoxaline-4-amines as antidepressants and antifatigue agents. U.S. Pat. No. 4,053,600 discloses 5-substituted[1,2,4]triazolo [4,3-c]quinazolines as hypotensives and anti-inflammatories.

European application No. 181,282 discloses [1,2,4]triazolo[1,5-c]quinazolin-5(6H)-ones as benzodiazepine antagonists and anxiomodulators.

SUMMARY OF THE INVENTION

The present invention concerns compounds of the formula

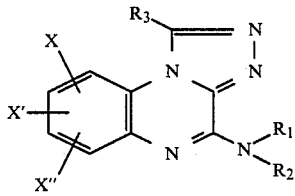

and the pharmaceutically acceptable acid addition salts thereof wherein $R_1$ is hydrogen, lower alkyl of from one to six carbon atoms, or alkanoyl of from two to five carbon atoms;

$R_2$ is phenyl optionally substituted by halogen or alkoxy of from one to three carbon atoms; cycloalkyl of from three to ten carbon atoms; bicycloalkyl of from seven to twelve carbon atoms; straight chain alkyl optionally substituted by OR' or NHR' wherein R' is hydrogen or lower alkyl; or —$(CH_2)_n$—NHR" wherein n is an integer of from two to twelve and R" is hydrogen, lower alkyl, alkanoyl, or aryl;

$R_3$ is hydrogen, straight or branched lower alkyl of from one to six carbon atoms, or a lower perfluoroalkyl of from one to three carbon atoms;

X, X', and X" are each independently hydrogen; halogen, OR, NHR wherein R is hydrogen, lower alkyl of from one to six carbon atoms, or acyl; trifluoroalkyl wherein the alkyl is from one to three carbon atoms.

Of particular interest in the present invention are compounds of formula I above where $R_1$ is hydrogen, $R_2$ is cycloalkyl and $R_3$, X, X', and X" are as defined above.

Of more particular interest in the present invention are compounds of formula I above where $R_1$ is hydrogen, $R_2$ is cyclopentyl, X, X', X", and $R_3$ are as defined above.

Of still more particular interest in the present invention are compounds of formula I above where $R_1$ is hydrogen, $R_2$ is cyclopentyl, X, X', and X" are hydrogen or halogen and $R_3$ is lower alkyl or trifluoromethyl.

Of most particular interest are the compound of formula I and being:

N-cyclopentyl[1,2,4triazolo[4,3-a]quinoxalin-4-amine;
N-cyclopentyl-1-methyl[1,2,4]triazolo[4,3-a]quinoxalin-4-amine;
N-cyclopentyl-1-ethyl[1,2,4]triazolo[4,3-a]quinoxalin-4-amine;
N-cyclopentyl-1-propyl[1,2,4]triazolo[4,3-a]quinoxalin-4-amine;
1-butyl-N-cyclopentyl[1,2,4]triazolo[4,3-a]quinoxalin-4-amine;
N-cyclopropyl-1-ethyl[1,2,4]triazolo[4,3-a]quinoxalin-4-amine;
N-cyclobutyl-1-ethyl[1,2,4]triazolo[4,3-a]quinoxalin-4-amine;
N-cyclohexyl-1-ethyl[1,2,4]triazolo[4,3-a]quinoxalin-4-amine;
exo-N-bicyclo[2.2.1]hept-2-yl-1-ethyl[1,2,4]triazolo [4,3-a]quinoxalin-4-amine;
(S)-1-[(1-ethyl[1,2,4]triazolo[4,3-a]quinoxalin-4-yl) amino]-2-propanol;
1-ethyl-N-phenyl[1,2,4]triazolo[4,3-a]quinoxalin-4-amine;
N-(4-chloro-2-methoxyphenyl)-1-ethyl[1,2,4]triazolo [4,3-a]quinoxalin-4-amine; and
N-cyclopentyl-1-(trifluoromethyl)[1,2,4]triazolo [4,3-a]quinoxalin-4-amine.

Another aspect of the present invention is a method for preparing compounds of formula I above which comprises:

(a) reacting a 2,3-dihaloquinoxaline with a hydrazine hydrate to form the corresponding 2-halo-3-hydrazinoquinoxaline;

(b) reacting that hydrazinoquinoxaline with a trialkylorthocarboxylate to form the corresponding 4-halo-1-alkyl[1,2,4]triazolo[4,3-a]quinoxaline; and (c) reacting that quinoxaline with a primary or secondary amine, $HNR_1R_2$ wherein $R_1$ and $R_2$ have the meaning discussed above, to form the desired $NR_1R_2$-1-alkyl[1,2,4]triazolo[4,3-a]quinoxaline, and converting this, if desired, to a pharmaceutically acceptable acid addition salt.

Another method for preparing certain compounds of formula I is also included in the present invention. It comprises:

(a) reacting the product of step (a) above, a 2-halo-3-hydrazinoquinoxaline, with trifluoroacetic acid to form the corresponding 4-hydroxy-1(trifluoromethyl)[1,2,4]-triazolo[4,3-a]quinoxaline;

(b) reacting that quinoxaline with phosphorus oxychloride and N,N-dimethylaniline to produce the corresponding 4-chloro-1-(trifluoromethyl)[1,2,4]-triazolo[4,3-a]quinoxaline;

(c) reacting that quinoxaline with a primary or secondary amine, such as $HNR_1R_2$ wherein $R_1$ and $R_2$ have meanings discussed above, to produce the corresponding $NR_1R_2$-1-(trifluoromethyl)[1,2,4]triazolo[4,3-a]quinoxaline, and converting this, if desired, to a pharmaceutically acceptable acid addition salt.

Still another aspect of the present invention is a pharmaceutical composition effective in treating depression which comprises an effective amount of a compound of formula I combined with a pharmaceutically acceptable carrier.

Still another aspect of the present invention is a pharmaceutical composition effective in treating fatigue which comprises an effective amount of a compound of formula I combined with a pharmaceutically acceptable carrier.

Still another aspect of the present invention is a pharmaceutical composition effective for increasing myocardial contractility of which comprises an effective amount of a compound of formula I combined with a pharmaceutically acceptable carrier.

Yet another aspect of the instant invention is a method of treating depression in a mammal in need of such treatment which comprises administering to a mammal an effective amount of a compound of formula I in unit dosage form.

Yet another aspect of the instant invention is a method of treating fatigue in a mammal in need of such treatment which comprises administering to a mammal an effective amount of a compound of formula I in unit dosage form.

Yet another aspect of the instant invention is a method of treating heart failure by increasing myocardial contractility in a mammal in need of such treatment which comprises administering to a mammal an effective amount of a compound of formula I in unit dosage form.

DETAILED DESCRIPTION

In the compounds of formula I as described above lower alkyl includes a straight or branched alkyl having from one to six carbon atoms. Lower perfluoroalkyl therefore includes perfluoroalkyls having from one to six carbon atoms, for example, trifluoromethyl.

Alkanoyl includes

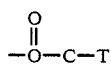

wherein T is an alkyl group of from one to five carbon atoms.

Alkoxy includes groups alkyl-O wherein the alkyl is from one to six carbon atoms as defined above.

Cycloalkyl includes groups of from three to ten carbon atoms inclusive of a saturated ring system including such rings as cyclopropyl, cyclobutyl, cyclopentyl, cyclohexyl and the like. Each ring may be substituted or unsubstituted by a straight or branched lower alkyl group.

Bicycloalkyl includes groups of from seven to twelve carbon atoms inclusive of, for example, bicyclo[2.2.1-]heptane, bicyclo[3.1.1.]heptane, bicyclo[3.2.1]octane, bicyclo[2.2.2]octane, bicyclo[6.1.0]nonane and bicyclo[5.3.0]deca-2,4,6, 8–10 pentaene.

Halogen includes particularly fluorine, chlorine, and bromine.

Appropriate pharmaceutically acceptable salts within the scope of the instant invention are those derived from mineral or organic acids such as hydrochloric acid, sulfuric acid, phosphoric acid, acetic acid, citric acid, oxalic acid, malonic acid, salicyclic acid, malic acid, fumaric acid, succinic acid, ascorbic acid, malcic acid, methaxsulfonic acid, burzenosulfonic acid, p-toluenesulfonic acid, and the like.

The acid addition salts of the basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

Certain compounds of the invention may contain assymetric carbon atoms and may exist in optical isomeric forms. For purposes of the invention, the individual pure isomers as well as mixtures thereof are considered to be equivalent.

The compounds of this invention may also exist in unsolvated as well as solvated forms, including hydrated forms. In general the solvated forms, with pharmaceutically acceptable solvents such as water ethanol and the like are equivalent to the unsolvated forms for purposes of the invention.

The compounds of the present invention may be prepared, in general, according to the schematic processes depicted in Schemes I and II.

Compounds of formula I may conveniently be synthesized by the following method. A 2,3-dihaloquinoxaline in an inert solvent such as ethanol is stirred vigorously with hydrazine hydrate at 15° to 25° C. for about fourteen to twenty hours. The resulting 2-halo-3-hydrazinoquinoxaline is reacted with a trialkylorthocarboxylic acid ester at about 100° C. for approximately one hour. Preferred esters are the triethyl- and trimethyl esters such as triethylorthoformate, triethylorthoacetate, triethylorthopropionate, trimethylorthovalerate or triethylorthobutyrate. The produce, a 4-halo-1-alkyl-[1,2,4]triazolo[4,3-a]quinoxaline, is reacted with an amine in a solvent such as DMF at close to room temperature for about three hours to produce the compounds of the instant invention. If desired, the compounds may be converted to their pharmaceutically acceptable salts. The reacton is illustrated in Scheme I below.

Scheme I

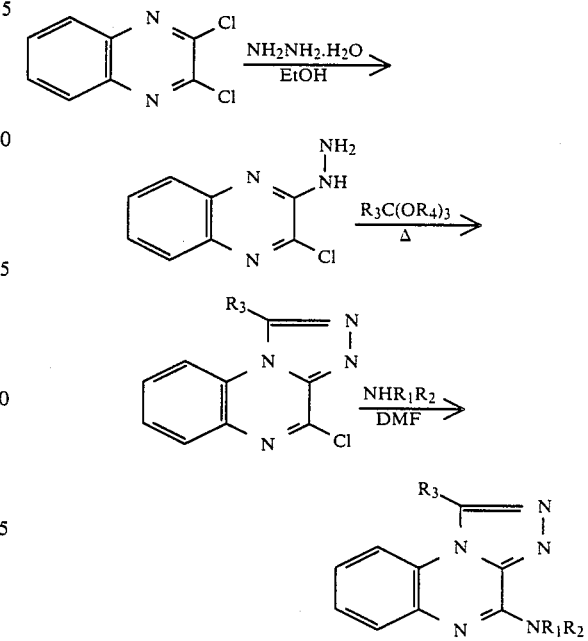

$R_4$ is a leaving group $R_1$, $R_2$, and $R_3$ have the meanings above. In addition to the above method, compounds of formula 1 may be prepared by a second route. A 2-halo-3-hydrazinoquinoxaline is reacted with trifluoroacetic acid at about 100° C. for approximately three hours producing the corresponding 1-trifluoromethyl[1,2,4]-triazolo[4,3-a]quinoxaline-4-ol. To a suspension of this compound in acetonitrile a quaternary amine chloride is added together with N,N-dimethylaniline and POCl₃. The preferred quaternary amine chloride is tetraethyl ammonium chloride. This reaction mixture is refluxed for about twenty hours producing 4-chloro-1-trifluoromethyl[1,2,4]triazolo[4,3-a]quinoxaline. This product is stirred with an amine in an inert solvent such as DMF at about 15° to 25° C. for from fourteen to eighteen hours producing compounds of the present invention. These may be converted, if desired, to a pharmaceutically acceptable acid addition salt. This reaction sequence is illustrated in Scheme II below.

Scheme II

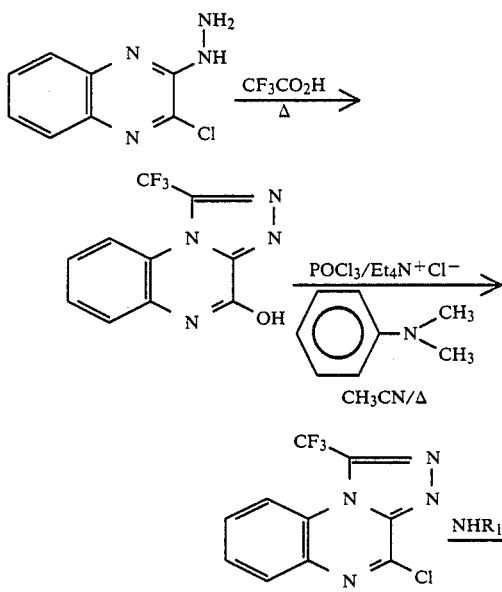

PHARMACOLOGICAL EVALUATION

Adenosine Receptor Binding—A₁ Receptor Affinity (RBA1)

Preparation of Membranes

Whole brain minus cerebellum and brainstem from male Long-Evans rats (150–200 g) is homogenized in 30 volumes of ice-cold 0.05 M Tris-HCl buffer pH 7.7 using a Brinkman Polytron PT-10, (setting number 6 for 20 seconds) and centrifuged for ten minutes at 20,000×g (Sorvall RC-2), 4° C. The supernatant is discarded, and the pellet is resuspended and centrifuged as before. The pellet is resuspended in 20 ml Tris-HCl buffer containing two International Units/ml of adenosine deaminase (Sigma type III from calf intestinal mucosa), incubated at 37° C. for 30 minutes, then subsequently at 0° C. for ten minutes. The homogenate is again centrifuged, and the final pellet is resuspended in ice-cold 0.05 M Tris-HCl buffer pH 7.7 to a concentration of 20 mg/ml original wet tissue weight and used immediately.

Assay Conditions

Tissue homogenate (10 mg/ml) is incubated in 0.05 M Tris-HCl buffer pH 7.7 containing 1.0 nM [³H]-N6-cyclohexyladenosine ([³H]-CHA) with or without test agents in triplicate for one hour at 25° C. Incubation volume was 2 ml. Unbound [³H]-CHA is separated by rapid filtration under reduced pressure through Whatman glass fiber (GF/B) filters. The filters are rinsed three times with 5 ml of ice-cold 0.05 M Tris-HCl buffer pH 7.7. The radio-labeled ligand retained on the filter is measured by liquid scintillation spectrophotometry after shaking the filters for one hour or longer on a mechanical shaker in 10 ml of Beckman Ready-Solv HP scintillation cocktail.

Calculations

Nonspecific binding is defined as the binding which occurs in the presence of 1 mM theophylline. The concentration of test agent which inhibited 50% of the specific binding (IC$_{50}$) is determined by nonlinear computer curve fit. The Scatchard plot is calculated by linear regression of the line obtained by plotting the amount of radioligand bound (pmoles/gram of tissue) versus $$\left[ \frac{\text{bound radioligand}}{\text{free radioligand}} \right].$$

Since the amount of radioligand bound is a small fraction of the total amount added, free radioligand is defined as the concentration of (nM) of radioligand added to the incubation mixture. The Hill coefficient is calculated by linear regression of the line obtained by plotting the log of the bound radioligand vs the log of the $$\left[ \frac{\text{bound radioligand}}{B_{max} - \text{bound radioligand}} \right].$$

The maximal number of binding sites (B$_{max}$) is calculated from the Scatchard plot.

Adenosine Receptor Binding—A₂ Receptor Affinity (RBA2)

Tissue Preparation

Brains from 200–500 g mixed sex Sprague-Dawley rats are purchased from Pel-Freez (Rogers, Arkansas). Fresh brains from male Long-Evans hooded rats (Blue Spruce Farms, Altamont, NY) give essentially identical results. Brains are thawed and then kept on ice while the striata are dissected out. Striata are disrupted in 10 vol of ice-cold 50 mM Tris.HCl (pH 7.7 at 25° C., pH 8.26 at 5° C.) (Tris) for 30 seconds in a Polytron PT-10 (Brinkman) at setting 5. The suspension is centrifuged at 50,000 xg for ten minutes, the supernatant discarded, the pellet resuspended in 10 vol ice-cold Tris as above, recentrifuged, resuspended at 1 g/5 ml, and stored in plastic vials at −70° C. (stable for at least six months). When needed, tissue is thawed at room temperature, disrupted in a Polytron, and kept on ice until used.

Incubation Conditions

All incubations are for 60 minutes at 25° C. in 12×75 mm glass tubes containing 1 ml Tris with 5 mg original tissue weight of rat weight of rat striatal membranes, 4 nM [³H]-N-ethyl adenosine-5'-carboxamide ([³H]NECA), 50 nM N6-cyclopentyladenosine (to eliminate A₁ receptor binding), 10 mM MgCl₂, 0.1 units/ml of adenosine deaminase and 1% dimethylsulfoxide. N6-Cyclopentyladenosine is dissolved at 10 mM in 0.02 N HCl and diluted in Tris. Stock solutions and dilutions of N6-cyclopentyladenosine can be stored at −20° C. for several months. Test compounds are dissolved at 10 mM in dimethylsulfoxide on the same day as the experiment, and diluted in dimethylsulfoxide to 100× the final incubation concentration. Control incubations receive an equal volume (10 μl) of dimethylsulfoxide; the resulting concentration of dimethylsulfoxide does not affect binding. [$^3$H]NECA is diluted to 40 nM in Tris. The membrane suspension (5 mg/0.79 ml) contained sufficient MgCl$_2$ and adenosine deaminase to give 10 mM and 0.1 units/ml, respectively, final concentration in the incubation. For test compounds with IC$_{50}$ values less than 1 μM, the order of additions is test compound (10 μl), N6-cyclopentyladenosine (100 μl), [$^3$H]NECA (100 μl), and membranes (0.79 ml). For test compounds with IC$_{50}$ values greater than 1 μM and limited water solubility, the order of additions (same volumes) is test compound, membranes, N6-cyclopentyladenosine, and [$^3$H]NECA. After all additions, the rack of tubes is vortexed, and the tubes are then incubated for 60 min at 25° C. in a shaking water bath. The rack of tubes is vortexed an additional time halfway through the incubation.

Incubations are terminated by filtration through 2.4 cm GF/B filters under reduced pressure. Each tube is filtered as follows: the contents of the tube are poured on the filter, 4 ml of ice-cold Tris are added to the tube and the contents poured onto the filter, and the filter is washed twice with 4 ml of ice-cold Tris. The filtration is complete in about twelve seconds. Filters are put in scintillation vials, 8 ml of Formula 947 scintillation fluid added, and the vials left overnight, shaken, and counted in a liquid scintillation counter at 40% efficiency.

Data Analysis

Nonspecific binding is defined as binding in the presence of 100 μM N6-cyclopentyladenosine, and specific binding is defined as total binding minus nonspecific binding. The IC$_{50}$ is calculated by weighted nonlinear least squares curve-fitting to the mass-action equation.

$$Y = T - S \cdot \frac{D}{D + K}$$

where
Y is cpm bound
T is cpm total binding without drug
S is cpm specific binding without drug
D is the concentration of drug
and
K is the IC$_{50}$ of the drug Weighting factors are calculated under the assumption that the standard deviation was proportional to the predicted value of Y. Nonspecific binding is treated as a very large (infinite) concentration of drug in the computer analysis.

The IC$_{50}$ values (nM) for adenosine A$_1$ and A$_2$ receptor affinity are reported in the Table I.

TABLE I

| Example | Receptor Binding Data | |
|---|---|---|
| | RBA-1 (nM) | RBA-2 (nM) |
| 1 | 331 | 7770 |
| 2 | 71 | 6130 |
| 3 | 49.7 | 2510 |
| 4 | 68 | 5080 |
| 5 | 101 | >100000 |
| 6 | 487 | 6630 |
| 7 | 109 | 2320 |
| 8 | 146 | 5880 |
| 9 | 74 | 8690 |
| 10 | 554 | 40700 |
| 11 | 982 | 20000 |

TABLE I-continued

| Example | Receptor Binding Data | |
|---|---|---|
| | RBA-1 (nM) | RBA-2 (nM) |
| 13 | 12.5 | 2080 |

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium sterate, talc, sugar, lactose, pectin, dextrin, starch, gelatin, tragacanth, methylcellulose, sodium carboxymethylcellulose, a low melting wax, cocoa butter, and the like. The term 'preparation' is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 1 mg to 500 mg preferably from 5 to 100 mg according to the particular application and the potency of the active ingredient. The compositions can, if desired, also contain other compatible therapeutic agents.

In therapeutic use as described above, the mammalian dosage range for a 70 kg subject is from 0.01 to 150 mg/kg of body weight per day or preferably 1 to 50 mg/kg of body weight per day. The dosages, however, may be varied depending upon the requirements of the patient, the severity of the condition being treated, and the compound being employed.

Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The compounds of formula I have been found to possess differing affinities for adenosine receptors, $A_1$ and $A_2$. The compounds of the invention are useful as antidepressants, antifatigue agents and as agents to increase myocardial contractility.

The following examples are merely illustrative of the present invention. They are not intended to in any way limit the scope thereof.

PREPARATION OF STARTING MATERIALS

EXAMPLE A

2-Chloro-3-hydrazinoquinoxaline

To a suspension of 2,3-dichloroquinoxaline (33.5 g; 0.168 mole) in 500 ml ethanol, hydrazine hydrate (18.5 g; 0.37 mole) was added and the reaction mixture was stirred vigorously at room temperature for 16 hours. The thick slurry was filtered, washed with ethanol to give 23.7 g of 2-chloro-3-hydrazinoquinoxaline having a mp of 181°–182° C. (dec.).

EXAMPLE B

4-Chloro[1,2,4]triazolo[4,3-a]quinoxaline

A reaction mixture of 4 g of 2-chloro-3-hydrazinoquinoxaline in 40 ml of triethyl orthoformate was heated at 100° C. for one hour. Upon cooling, the precipitated solid was filtered, washed with cyclohexane, and dried to give 3.9 g of 4-chloro[1,2,4]-triazolo[4,3-a]quinoxaline having a mp of 287°–290° C.

EXAMPLE C

4-Chloro-1-methyl[1,2,4]triazolo[4,3-a]quinoxaline

A reaction mixture of 5 g of 2-chloro-3-hydrazinoquinoxaline in 50 ml of triethyl orthoacetate was heated at 100° C. for three hours. Upon cooling, the precipitated solid was filtered, washed with cyclohexane, and dried affording 4.27 g of 4-chloro-1-methyl[1,2,4]triazolo[4,3-a]quinoxaline having a mp of 215°–218° C.

EXAMPLE D

4-Chloro-1-ethyl[1,2,4]triazolo[4,3-a]quinoxaline

The title compound was prepared essentially as described in Example 2 substituting triethyl orthopropionate for triethyl orthoformate; mp 158°–160° C.

EXAMPLE E

1-Butyl-4-chloro[1,2,4]triazolo[4,3-a]quinoxaline

The title compound was prepared essentially as described in Example 3 substituting trimethyl orthovalerate for triethyl orthoacetate; mp 144°–146° C.

EXAMPLE F

4-Chloro-1-propyl[1,2,4]triazolo[4,3-a]quinoxaline

A reaction mixture of 5 g of 2-chloro-3-hydrazinoquinoxaline in 15 ml of triethyl orthobutyrate was heated at 100° C. for three hours. Upon cooling, the precipitated solid was filtered, washed with cyclohexane, and dried giving 4.0 g of 4-chloro-1-propyl[1,2,4]-triazolo[4,3-aquinoxaline having a mp of 172°–175° C.

EXAMPLE 1

N-Cyclopentyl[1,2,4]triazolo[4,3-a]quinoxalin-4-amine

A reaction mixture of 4-chloro[1,2,4]triazolo 4,3-a]quinoxaline (1.0 g; 0.0049 mole) and cyclopentanamine (1.25 g; 0.014 mole) in 15 ml of DMF was stirred at room temperature for three hours. The precipitated solid was filtered, washed with cyclohexane, and dried affording 0.95 g (76%) of N-cyclopentyl[1,2,4]triazolo[4,3-a]quinoxalin-4-amine having a mp of 257°–260° C.

Analysis Calcd. for $C_{14}H_{15}N_5$
C, 66.38; H, 5.96; N, 27.64
Found C, 66.55; H, 5.98; N, 27.76.

EXAMPLE 2

N-Cyclopentyl-1-methyl]1,2,4]triazolo[4,3-a]
quinoxalin-4-amine

A reaction mixture of 4-chloro-1-methyl[1,2,4]-triazolo[4,3-a]quinoxaline (1.0 g; 0.004 mole) and cyclopentanamine (1.17 g; 0.013 mole) in 15 ml of DMF was stirred at room temperature for 20 hours. The reaction mixture was poured over ice-water and the precipitated solid was filtered, washed with water and dried affording 0.9 g (74%) of N-cyclopentyl-1methyl-[1,2,4]triazolo[4,3-a]quinoxalin-4-amine having a mp of 196°–198° C.

Analysis Calcd. for $C_{15}H_{17}N_5$
C, 67.39; H, 6.40; N, 26.19
Found C, 67.29; H, 6.10; N, 26.05.

EXAMPLE 3

N-Cyclopentyl-1-ethyl[1,2,4]triazolo[4,3-a]quinoxalin-4-amine

The title compound was prepared essentially as described in Example 2 substituting 4-chloro-1-ethyl[1,2,4]triazolo[4,3-a]quinoxaline for 4-chloro-1-methyl[1,2,4]triazolo[4,3-]quinoxaline; mp 166°–168° C.

Analysis Calcd. for $C_{16}H_{19}N_5$
C, 68.30; H, 6.80; N, 24.89
Found C, 68.25; H, 6.66; N, 24.62.

EXAMPLE 4

N-Cyclopentyl-1-propyl[1,2,4]triazolo[4,3-a]quinoxalin-4-amine

A reaction mixture of 4-chloro-1-propyl[1,2,4]triazolo[4,3-a]quinoxaline (1.0 g; 0.004 mole) and cyclopentanamine (1.0 g; 0.012 mole) in 15 ml of DMF was stirred at room temperature for 20 hours. The precipitated solid was filtered, washed with ethanol, and dried affording 0.98 g (82%) of N-cyclopentyl-1-propyl[1,2,4]triazolo[4,3-a]quinoxalin-4-amine having a mp of 186°–188° C.

Analysis Calcd. for $C_{17}H_{21}N_5$
C, 69.12; H, 7.16; N, 23.70
Found C, 68.98; H, 7.11; N, 23.54.

EXAMPLE 5

1-Butyl-N-cyclopentyl[1,2,4]triazolo[4,3-a]quinoxalin-4-amine

The title compound was prepared essentially as described in Example 4 substituting 4-chloro-1-butyl[1,2,4]triazolo[4,3-a]quinoxaline for 4-chloro-1-propyl[1,2,4]triazolo[4,3-a]quinoxaline; mp 195°–197° C.

Analysis Calcd. for $C_{18}H_{23}N_5$
C, 69.87; H, 7.49; N, 22.63
Found C, 69.75; H, 7.43; N, 22.60.

EXAMPLE 6

N-Cyclopropyl-1-ethyl[1,2,4]triazolo[4,3-a]quinoxalin-4-amine

The title compound was prepared essentially as described in Example 4 substituting 4-chloro-1-ethyl[1,2,4]triazolo[4,3-a]quinoxaline and cyclopropyl amine for 4-chloro-1-n-propyl[1,2,4]triazolo[4,3-a]quinoxaline and cyclopentanamine respectively; mp 190°–192° C.

Analysis Calcd. for $C_{14}H_{15}N_5$
C, 66.38; H, 5.96; N, 27.64
Found C, 66.04; H, 6.11; N, 27.63.

EXAMPLE 7

N-Cyclobutyl-1-ethyl[1,2,4]triazolo[4,3-a]quinoxalin-4-amine

The title compound was prepared essentially as described in Example 2 substituting 4-chloro-1-ethyl[1,2,4]triazolo[4,3-a]quinoxaline and cyclobutyl amine for 4-chloro-1-methyl[1,2,4]triazolo[4,3-a]quinoxaline and cyclopentanamine respectively; mp 215°–217° C.

Analysis Calcd. for $C_{15}H_{17}N_5$
C, 67.39; H, 6.40; N, 26.19
Found C, 67.04; H, 6.36; N, 25.91.

EXAMPLE 8

N-Cyclohexyl-1-ethyl[1,2,4]triazolo[4,3-a]quinoxalin-4-amine

The title compound was prepared essentially as described in Example 4 substituting 4-chloro-1-ethyl[1,2,4]triazolo[4,3-a]quinoxaline and cyclohexanamine for 4-chloro-1-propyl[1,2,4]triazolo [4,3-a]quinoxaline and cyclopentanamine respectively; mp 217°–220° C.

Analysis Calcd. for $C_{17}H_{21}N_5$
C, 69.12; H, 7.16; N, 23.70
Found C, 69.28; H, 7.28; N, 23.77.

EXAMPLE 9

Exo-N-bicyclo[2.2.1]hept-2-yl-1-ethyl[1,2,4]triazolo[4,3-a]quinoxalin-4-amine

The title compound was prepared essentially as described in Example 2 substituting 4-chloro-1-ethyl[1,2,4]triazolo[4,3-a]quinoxaline and exo-bicyclo[2.2.1]heptan-2-amine for 4-chloro-1-methyl[1,2,4]triazolo[4,3-a]quinoxaline and cyclopentanamine respectively; mp 170°–172° C.

Analysis Calcd. for $C_{15}H_{21}N_5$
C, 70.33; H, 6.88; N, 22.78
Found C, 70.27; H, 6.93; N, 22.84.

EXAMPLE 10

(S)-1- (1-ethyl[1,2,4]triazolo[4,3-a]quinoxalin-4-yl)amino]-2-propanol

The title compound was prepared essentially as described in Example 4 substituting 4-chloro-1-ethyl[1,2,4]triazolo[4,3-a]quinoxaline and (S)-1-amino-2-propanol for 4-chloro-1-propyl[1,2,4]triazolo[4,3-a]quinoxaline and cyclopentanamine respectively; mp 120°–123° C.

Analysis Calcd. for $C_{14}H_{17}N_5$
C, 61.97; H, 6.31; N, 25.81
Found C, 62.00; H, 6.48; N, 25.52.

EXAMPLE 11

1-Ethyl-N-phenyl[1,2,4]triazolo[4,3-a]quinoxalin-4-amine

The title compound was prepared essentially as described in Example 2 substituting 4-chloro-1-ethyl[1,2,4]triazolo[4,3-a]quinoxaline and benzenamine for 4-chloro-1-methyl[1,2,4]triazolo[4,3-a]quinoxaline and cyclopentanamine respectively; mp 172°–174° C.

Analysis Calcd. for $C_{17}H_{15}N_5$
C, 70.57; H, 5.22; N, 24.20
Found C, 70.30; H, 5.26; N, 24.02.

EXAMPLE 12

N-(4-Chloro-2-methoxyphenyl)-1-ethyl[1,2,4]triazolo[4,3-a]quinoxalin-4-amine

The title compound was prepared essentially as described in Example 2 substituting 4-chloro-1-ethyl[1,2,4]triazolo[4,3-a]quinoxaline and 2-methoxy-4-chlorobenzenamine for 4-chloro-1-methyl1,2,4]- triazolo[4,3-a]quinoxaline and cyclopentanamine respectively; mp 245°–248° C.

Analysis Calcd. for $C_{18}H_{16}N_5OCl.0.25H_2O$
C, 60.34; H, 4.64; N, 19.54; Cl, 9.89
Found C, 60.51; H, 4.68; N, 19.29; Cl, 10.01.

EXAMPLE 13

N-Cyclopentyl-1-(trifluoromethyl)[1,2,4]triazolo[4,3-a]quinoxalin-4-amine a. 1-(trifluoromethyl)[1,2,4]triazolo[4,3-a]quinoxalin-4-ol

2-Chloro-3-hydrazinoquinoxaline [3.8 g; 0.02 mole] was added to 15 ml of ice-cold trifluoroacetic acid. Reaction was then heated at 100° C. for three hours and poured over ice-water. Precipitated solid was filtered, washed with water, and dried affording 3.7 g of 1-(trifluoromethyl)[1,2,4]triazolo[4,3-a]quinoxalin-4-ol having a mp of >325° C.

b. 4-Chloro-1-(trifluoromethyl)[1,2,4]triazolo[4,3-a]quinoxaline

To a suspension of 1-(trifluoromethyl)[1,2,4]triazolo[4,3-a]quinoxalin-4-ol (2.5 g; 0.01 mole) in 60 ml of acetonitrile, $Et_4N^+Cl^-$ (2.4 g) followed by N,N-dimethylaniline (1.7 ml) and $POCl_3$ (3.75 ml) were added. Reaction mixture was refluxed for 20 hours. Volatiles were removed under reduced pressure, residue was dissolved in $CHCl_3$ (100 ml) and added to the ice-water. Layers were separated, the aqueous layer was extracted with chloroform (2×200 ml). The combined extract was washed with 5% $NaHCO_3$ (2×120 ml) followed by brine (2×50 ml). It was dried over $MgSO_4$, filtered, and volatiles were removed. The residue was crystallized from chloroform-hexane affording 1.78 g of 4-chloro-1-(trifluoromethyl)[1,2,4]triazolo[4,3-a]quinoxaline; mass spectrum m/e, 272 (m+).

c. 4-Cyclopentyl-1-(trifluoromethyl)[1,2,4]triazolo[4,3-a]quinoxalin-4-amine A solution of 4-chloro-1-(trifluoromethyl)[1,2,4]triazolo[4,3-a]quinoxaline (1.5 g; 0.005 mole) and cyclopentanamine (1.0 g; 0.011 mole) in 20 ml of DMF was stirred at room temperature for 16 hours. It was added to ice-water. Precipitated solid was filtered, dissolved in 100 ml chloroform, washed with brine (1×25 ml), dried over $MgSO_4$, filtered, and volatiles were removed. It was dissolved in ether-2-propanol and diluted with hexane. Solid material obtained was filtered and dried affording 0.85 g of 4-cyclopentyl-1-(trifluoromethyl)[1,2,4]triazolo[4,3-a]quinoxalin-4-amine having a mp of 183°–184° C.

Analysis Calcd. for $C_{15}H_{14}N_5F_3$
C, 56.07; H, 4.39; N, 21.79
Found C, 55.92; H, 4.36; N, 21.92.

I claim:

1. A compound named exo-N-bicyclo[2.2.1]hept-2-yl-1-ethyl[1,2,4]-triazolo [4,3-a]quinoxalin-4-amine.

2. A compound named N-(4-chloro-2-methoxyphenyl)-1-ethyl[1,2,4]-triazolo[4,3-a]quinoxolin-4-amine.

3. A method of treating heart failure by increasing myocardial contractility in mammals which comprises administering to said mammals a pharmaceutical composition comprising an effective amount of a compound of formula

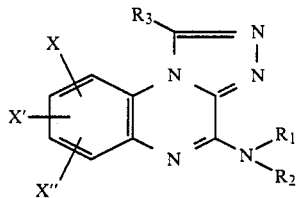

wherein $R_1$ is hydrogen;
$R_2$ is phenyl optionally substituted by halogen or alkoxy of from one to three carbon atoms; cycloalkyl of from three to ten carbon atoms; bicycloalkyl of from seven to twelve carbon atoms; straight chain alkyl substituted by Or' or NHR' wherein R' is hydrogen or lower alkyl; or —$(CH_2)_n$—NHR'' wherein n is an integer of from two to twelve and R'' is hydrogen, lower alkyl, alkanoyl, or aryl;
$R_3$ is hydrogen, straight or branched lower alkyl of from one to six carbon atoms, or a lower perfluoroalkyl of from one to three carbon atoms;
X, X', and X'' are each independently hydrogen; halogen; OR, NHR wherein R is hydrogen, lower alkyl of from one to six carbon atoms, or acyl; trifluoralkyl wherein the alkyl is from one to three carbon atoms; or —$SO_2NHR'''$ wherein R''' is hydrogen or lower alkyl of from one to six carbon atoms, or a pharmaceutically acceptable acid addition salt thereof combined with a pharmaceutically acceptable carrier in unit dosage form.

4. A compound of the formula

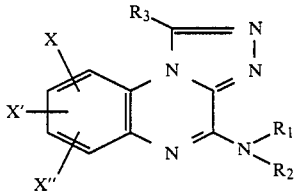

wherein $R_1$ is hydrogen;
$R_2$ is bicycloalkyl of from seven to twelve carbon atoms;
$R_3$ is hydrogen, straight or branched lower alkyl of from one to six carbon atoms, or a lower perfluoroalkyl of from one to three carbon atoms;
X, X', and X'' are each independently hydrogen; halogen; OR, NHR wherein R is hydrogen, lower alkyl of from one to six carbon atoms, or acyl; trifluoroalkyl wherein the alkyl is from one to three carbon atoms; or —$SO_2NHR'''$ wherein R''' is hydrogen or lower alkyl of from one to six carbon atoms, or a pharmaceutically acceptable acid addition salt thereof.

* * * * *